United States Patent [19]

Miyazaki et al.

[11] Patent Number: 5,376,640
[45] Date of Patent: Dec. 27, 1994

[54] LIPOLYTIC ENZYME INHIBITORS

[75] Inventors: Toshiyuki Miyazaki; Hirofumi Motoi, both of Kawagoe; Toshiaki Kodama, Wako; Taturo Maeda, Saitama; Takahiro Tsujita, Ehime; Hiromichi Okuda, Matsuyama, all of Japan

[73] Assignee: Nisshin Flour Milling Co., Ltd., Tokyo, Japan

[21] Appl. No.: 973,852

[22] Filed: Nov. 9, 1992

Related U.S. Application Data

[60] Division of Ser. No. 950,773, Sep. 24, 1992, which is a continuation of Ser. No. 631,321, Dec. 20, 1990, abandoned.

[30] Foreign Application Priority Data

| Dec. 25, 1989 | [JP] | Japan | 1-332884 |
| Mar. 27, 1990 | [JP] | Japan | 2-75600 |
| Jul. 25, 1990 | [JP] | Japan | 2-194782 |

[51] Int. Cl.$^5$ ............ A61K 37/02; A61K 37/64
[52] U.S. Cl. ............ 514/12; 514/13; 514/14; 514/15; 514/16; 514/17; 514/18; 514/563; 514/909
[58] Field of Search .......... 530/358, 372, 375, 328, 530/329, 330, 332; 435/197, 198; 514/2, 8, 563, 564, 565, 772.3, 773, 784, 788, 909, 911, 950, 12, 13, 14, 15, 16, 17, 18; 562/561, 562

[56] References Cited

U.S. PATENT DOCUMENTS

| 3,867,365 | 2/1975 | Stahman et al. | 530/327 |
| 4,287,185 | 9/1981 | Toyoshima et al. | 530/330 |
| 4,598,089 | 7/1986 | Hadvary et al. | 435/886 |
| 4,803,224 | 2/1989 | Tenmyo et al. | 435/129 |
| 4,818,763 | 4/1989 | Rusch et al. | 530/358 |
| 4,867,974 | 9/1989 | Fujii et al. | 530/300 |
| 5,009,907 | 4/1991 | Fujii et al. | 426/335 |

FOREIGN PATENT DOCUMENTS

| 15263/88 | 11/1988 | Australia . |
| 61-57840 | 12/1986 | Japan . |

OTHER PUBLICATIONS

Agric. Biol. Chem., vol. 41, No. 9, issued 1977, Shima et al., "Polylysine Produced by Streptomyces", pp. 1807-1809.

Biochemistry Correlations, Devlin ed. John Wiley & Sons, 1982. pp. 1162-1164.

Journal of Lipid Research, vol. 25, 1984, pp. 1214-1221, Y. Gargouri, et al., "Studies on the Inhibition of Pancreatic and Microbial Lipases by Soybean Proteins".

J. Agric. Food Chem, vol. 26, No. 4, 1978, pp. 794-796, C. Hernandez-Lucas, et al., "Identification and Purification of a Purothionin Homologue from Rye (Secale Cereale L.)".

Agr. Biol. Chem., vol. 34, No. 7, pp. 1089-1094, 1970, T. Okada, et al., "A Lethal Toxic Substance for Brewing Yeast in Wheat and Barley".

(List continued on next page.)

Primary Examiner—Jeffrey E. Russel
Attorney, Agent, or Firm—Oblon, Spivak, McClelland, Maier & Neustadt

[57] ABSTRACT

A method of inhibiting enzymatic hydrolysis of lipids in a mammal concerns orally administering an effective amount of a purothionin or an ε-polylysine of the formula:

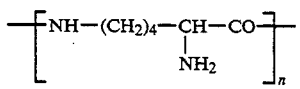

or a salt thereof, wherein n is a number of from 5 to 9, to a mammal in need thereof. Alternatively, the method concerns orally administering an ε-polylysine of the formula above or a salt thereof, wherein n is a number of from 4 to 30, to a mammal suffering from lipemia or obesity. The purothionin, ε-polylysine or salt thereof is a lipolytic enzyme inhibitor, useful as a dieting agent, an agent for the prevention of obesity and lipemia, and as an additive for food and feed.

7 Claims, No Drawings

OTHER PUBLICATIONS

Febs. Lett. 1975, 53 (1), 1–4 Isolation of C-I and C-II activate lipoprotein lipases and protamine.

Plant Science 1989, 59, 35–43 Phospholipase D of rice bran. II The effects of the enzyme inhibitors and . . . .

Aust J Biol Sci 1983, 36, 41–48 Lipoprotein Lipase of Sheep and Rat Adipose Tissues.

Acta Cuient Venezolana 1979, 30, 152–161 The cafactor effects of serum lipoproteins on lipoprotein lipase activity and . . . .

J Dairy Sci. 1976, 59 (7), 1203–1214 Milk Protein Lipases: A Review.

Biokhimiya 1985, 50(5), 804–813 Inhibition of lipoprotein lipolysis by polyarginine and study on the . . . .

S. Budavari et al.: "The Merck Index", edition No. 11, 1989, Merck & Co., Rahway, N.J., US-pp. 1263–1264, ref. No. 7961.

Chemical Abstracts, vol. 103, No. 7, 19 aout 1985, p. 243, resume No. 50279p, Columbus, Ohio, US; A. N. Klimov et al: "Inhibition of lipoprotein lipolysis by polyarginine and study of the mechanism of its interaction with lipoprotein lipase", & Biokhimiya (Moscow) 1985, 50(5), 804–13—En entier.

J. Agric Food Chem., vol. 37, No. 4, 1989, pp. 873–877, Washington, DC, US; D. Bercovici et al.: "Poly-L-lysine and multioligo (L-methionyl) poly-L-lysine as nutritional sources of essential amino acids"—En Entier.

French Search Document-Bureau D. A. Casalonga-Josse, 8, Avenue Percier 75008 Paris-No. 90 16069.

Chemical Abstracts vol. 112: 68564y (1990).

S. Budavari et al.: "The Merck Index", edition No. 11, 1989, Merck & Co., Rahway, N.J., US —p. 746, 43f. No. 4643.

Biological Abstracts, vol. 80, No. 3, 1985, p. AB-721, resume No. 24791, Philadelphia, PA, US; J. Harenberg et al.: "Inhibition of low molecular weight heparin by protamine chloride in vivo", & Throb. Res., 38(1): 11–20, 1985 -En entier.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Lys Ser Cys Cys Arg Ser Thr Leu Gly Arg Asn Cys Tyr Asn Leu Cys
 1               5                  10                  15
Arg Ala Arg Gly Ala Gln Lys Leu Cys Ala Gly Val Cys Arg Cys Lys
            20                  25                  30
Ile Ser Ser Gly Leu Ser Cys Pro Lys Gly Phe Pro Lys
            35                  40                  45
```

( 2 ) INFORMATION FOR SEQ ID NO:2:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Lys Ser Cys Cys Arg Thr Thr Leu Gly Arg Asn Cys Tyr Asn Leu Cys
 1               5                  10                  15
Arg Ser Arg Gly Ala Gln Lys Leu Cys Ser Thr Val Cys Arg Cys Lys
            20                  25                  30
Leu Thr Ser Gly Leu Ser Cys Pro Lys Gly Phe Pro Lys
            35                  40                  45
```

( 2 ) INFORMATION FOR SEQ ID NO:3:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Lys Ser Cys Cys Lys Ser Thr Leu Gly Arg Asn Cys Tyr Asn Leu Cys
 1               5                  10                  15
Arg Ala Arg Gly Ala Gln Lys Leu Cys Ala Asn Val Cys Arg Cys Lys
```

```
                    20                      25                      30
         Leu  Thr  Ser  Gly  Leu  Ser  Cys  Pro  Lys  Asp  Phe  Pro  Lys
                        35                       40                     45
```

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
         Lys  Lys  Lys  Lys
         1
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
         Lys  Lys  Lys  Lys  Lys
         1                    5
```

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2

( i x ) FEATURE:
        ( A ) NAME/KEY: Modified-site
        ( B ) LOCATION: 2..3

( i x ) FEATURE:
        ( A ) NAME/KEY: Modified-site
        ( B ) LOCATION: 3..4

( x i ) SEQUENCE DESCRIPTION: SEQ ID NO:6:

```
         Xaa  Xaa  Xaa  Xaa
         1
```

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..2

( i x ) FEATURE:
        ( A ) NAME/KEY: Modified-site
        ( B ) LOCATION: 2..3

( i x ) FEATURE:
        ( A ) NAME/KEY: Modified-site (B) LOCATION: 3..4

(ix) FEATURE:
(A) NAME/KEY: Modified-site
(B) LOCATION: 4..5

(xi) SEQUENCE DESCRIPTION: SEQ ID NO:7:

Xaa Xaa Xaa Xaa Xaa
 1                    5

LIPOLYTIC ENZYME INHIBITORS

This is a division of application Ser. No. 07/950,773, filed on Sep. 24, 1992, which is a continuation application of Ser. No. 07/631,321, filed Dec. 20, 1990, now abandoned.

BACKGROUND OF THE INVENTION

1. Field of the Invention

This invention relates to inhibitors of enzymes participating in lipolysis. More particularly the invention relates to lipolytic enzyme inhibitors which comprises basic proteins and/or basic polypeptides.

2. Description of the Prior Art

It has been reported in a number of references that proteins such as serum albumin, β-lactoglobulin and certain soybean proteins inhibit some kinds of lipases (see, for example, Journal of Lipid Research, Vol. 25, 1984, pages 1214–1221). In the presence of bile acids, however, these proteins lose their lipase inhibitory activity and do not function as a lipase inhibitor in vivo.

SUMMARY OF THE INVENTION

Our continuing study on the proteinaceous lipase inhibitors has revealed that basic proteins, basic peptides and the salts thereof inhibit or suppress the activity of lipolytic enzymes in the presence of bile acids.

Thus the present invention provides a lipolytic enzyme inhibitor which comprises as an active ingredient at least one of a basic protein, a basic peptide and salts thereof.

DETAILED DESCRIPTION OF THE INVENTION

The term "lipolytic enzyme inhibitor" as used herein refers to an agent having a function of inhibiting or suppressing the activity of lipolytic enzymes such as lipases, thereby inhibiting or suppressing hydrolysis of lipids which results in inhibiting or suppressing the intestinal absorption of lipids.

The lipolytic enzyme inhibitors of the present invention are effective in the condition where lipids are emulsified in the presence of bile acids, thus effectively acting in vivo.

The basic proteins, basic polypeptides and salts thereof which can be used in the invention include purothionins contained in wheat; purothionin analogues contained in other cereals than wheat (including barley and rye) such as purothionin-analogous polypeptides widely distributed in barley as disclosed in Japanese patent Publication No. 57840/1986 and purothionin-analogous polypeptides occurring in rye as disclosed in J. Agric. Food Chem., Vol. 26, No. 4, pages 794–796 (1978); protamine; histone; polylysine; polyarginine and salts thereof.

Three kinds of purothionin, α1-, α2-, β-purothionin have some differences in amino acid sequence, each having the following amino acid sequences respectively (SEQ ID NO:1), (SEQ ID NO:2) and (SEQ ID NO:3). Any purothionins can be used in the present invention.

There are known three types of protamines including mono-, di- and tri-protamines and five types of histones including H1, H2A, H2B, H3, H4 and H5. Any types of those can be used in the present invention.

Polylysine is distinguished by the site of peptide bond and composed of ε-polylysine represented by formula (I)

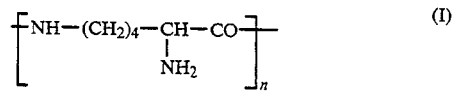

wherein n represents the degree of polymerization of lysine and α-polylysine represented by formula (II)

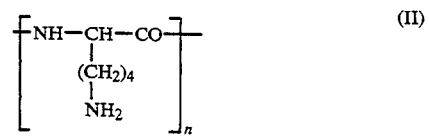

wherein n is as defined above. Any polylysines and salts thereof may be used in the invention. ε-Polylysine and its salts are preferred because they can maintain in vitro the function of suppressing or inhibiting the lipolytic enzymes over a longer period of time, thus leading to more reduced total lipid absorption as compared with α-polylysine, other basic proteins and polypeptides and salts thereof. Polylysines of formulas (I) and (II) wherein n is 4 or more, particularly 5 or more are more effective because of their higher activities of inhibiting lipolytic enzyme. ε-Polylysines wherein n is less than 9 have low antimicrobial activity. Thus ε-polylysines wherein n is 5–9 will have an effect on inhibition of lipid absorption without damage to intestinal flora.

The amino acids composing basic proteins and peptides include two kinds of optical isomers, L- and D-forms. The basic proteins and peptides derived from natural products are known to be usually composed of L-amino acids.

The basic proteins and polypeptides as well as salts thereof which are used in the invention may be composed of either or both of L- and D-amino acids.

The lipolytic enzyme inhibitors of the present invention may contain a basic protein, a basic peptide and salts thereof alone or in combination therewith.

The lipolytic enzyme inhibitors of the invention can be administered to human beings and various animals including livestock and poultry such as cattle, horse and chicken as well as pet animals such as dog and cat. The effective dose will vary depending on the type, age and physical conditions, etc. of the subjects to be administered. Preferably, they may be given at any suitable dose for individual subjects.

The lipolytic enzyme inhibitors of the invention is formulated into a preparation for oral administration. They may be administered either alone or in admixture with carrier conventionally used in pharmaceutical industry or in combination with other drugs. Furthermore, they can be used in any form of preparations such as tablets, granules, capsules, powders or the like.

In addition, the lipolytic enzyme inhibitors of the invention may also be administered as an additive for food and feed. Thus the inhibitors of the invention are useful as an additive for food and feed.

Administration of the lipolytic enzyme inhibitors of the invention to human beings and other animals can inhibit lipolytic enzymes to suppress or inhibit the hydrolysis of lipids so that rapid intestinal absorption of ingested lipids can be inhibited and total fat absorption can also be controlled at a low level, thereby achieving a variety of effects such as prevention of lipemia and obesity. Thus the inhibitors of the invention are useful as a dieting agent for the prevention of obesity and lipemia.

Of the lipolytic enzyme inhibitors of the invention, especially ε-polylysines maintain their lipid absorption-inhibitory actions in the living body over a long period of time, which result in largely reduced total fat absorption in vitro.

The invention is further illustrated by the following non-limitative examples.

EXAMPLE 1

Preparation of Purothionin

A crude purothionin mixture containing $\alpha_1$-, $\alpha_2$- and $\beta$-purothionins (SEQ ID NOS:1-3) was obtained starting from weak wheat flour according to the method described in Agr. Biol. Chem., Vol. 34, No. 7, pages 1089-1094 (1970). The resulting crude mixture was purified to isolate $\alpha_2$-purothionin (SEQ ID NO:2) and $\beta$-purothionin (SEQ ID NO:3), respectively.

Preparation of Olive Oil Emulsion 250 mg of an olive oil, 21.5 mg of sodium cholate as a bile acid component and 30 mg of phosphatidylcholine were added to 5 ml of a 300 mM potassium phosphate buffer solution at pH 6.8 (called hereafter "potassium phosphate buffer").

The mixture was ultrasonicated to prepare an olive oil emulsion.

Preparation of Protein (Polypeptide)-Containing Solution

One ml of the potassium phosphate buffer was added to each 4 mg of the crude purothionin mixture, the purified $\alpha_2$-purothionin (SEQ ID NO:2) and the purified $\beta$-purothionin (SEQ ID NO:3), bovine serum albumin (called hereafter "BSA", A7030, Sigma Co., Ltd., U.S.A.), $\beta$-lactoglobulin (L0130, Sigma Co., Ltd.) and ovalbumin (A5503, Sigma Co., Ltd.) to prepare six kinds protein (polypeptide)-containing solutions.

Preparation of Lipase Solution

Porcine pancreatic lipase (manufactured by Sigma Co., Ltd.) was added to the potassium phosphate buffer solution to prepare a lipase solution containing 100 units porcine pancreatic lipase per ml.

Assay of Lipase Inhibitory Activity of Proteins

The control and six test samples were prospered in the following manner.

100 μl of an olive oil emulsion as prepared above were used as a substrate.

50 μl of potassium phosphate buffer was added to the substrate to prepare an emulsion for control sample. Each 50 μl of the protein(polypeptide)-containing solutions as prepared above was added to 100 μl of the substrate to prepare six emulsions for test samples. All of the emulsions were incubated for 5 min. To each of those emulsions was added 50 μl of the lipase solution as prepared above. The resulting mixture was incubated at 37° C. for one hour, subsequently to which were added 3 ml of an extraction solvent (chloroform:methanol:n-heptane=49:1:49). After being shaken for 5 min., the mixture was centrifuged at 3000 rpm for 5 min. The upper layer was removed with an aspirator and to the remaining solution was added 1 ml of a copper reagent (0.45M triethanol amine, 0.05N acetic acid, 3,4% copper sulfate pentahydrate and 20% sodium chloride). The mixture was shaken for 5 min. and centrifuged at 3000 rpm for 5 min. 0.5 ml of a solution was taken from the upper layer and to the solution was added 0.5 ml of a color developing agent (a solution of 0.1% bathocuproine and 0.05% butyl hydroxyanisole in the above extraction solvent).

The resulting solutions for control and test samples were measured for the absorbance at 480 nm (A480) using a photometer to determine the amount of the free fatty acids as formed, i.e., the activity of the porcine pancreatic lipase.

The results are shown in Table 1 in which the activity is expressed in terms of the percentage of the Abs480 in the case where control sample was hydrolyzed by the porcine pancreatic lipase.

TABLE 1

| Protein (polypeptide) contained in samples | Isoelectric pH | Activity of porcine pancreatic lipase (%) |
|---|---|---|
| Control | — | 100 |
| Crude purothionins (SEQ ID NOS: 1-3) | Ca. 10 | 6.0 |
| $\alpha_2$-Purothionin (SEQ ID NO: 2) | Ca. 10 | 0 |
| $\beta$-Purothionin (SEQ ID NO: 3) | Ca. 10 | 0 |
| Ovalbumin | Ca. 4-5 | 107.0 |
| $\beta$-Lactoglobulin | Ca. 5 | 103.9 |
| BSA | Ca. 4-5 | 105.4 |

It is seen from the results shown in Table 1 that the lipase activity is much inhibited when the inhibitor of the invention comprising crude purothionins or a purified $\alpha_2$- purothionin (SEQ ID NO:2) or $\beta$-prothionin (SEQ ID NO:3) is added in the presence of bile acid, whereas ovalbumin, $\beta$-lactoglobulin and BSA, not belonging to basic proteins do not have lipase inhibitory activity under the specified condition in this example.

EXAMPLE 2

Activity of porcine pancreatic lipase was investigated in the same way as in Example 1 except that the crude purothionin- (SEQ ID NOS:1-3) or $\beta$-purothionin-containing (SEQ ID NO:3) solution was diluted to a protein concentration of 0.2 mg/ml. Lipase activity of the crude purothionin-containing (SEQ ID NOS:1-3) sample was 97.5%, thereby indicating that crude purothionin in such concentration has little inhibitory activity against porcine pancreatic lipase. On the contrary, the lipase activity of the $\beta$-purothionin-containing (SEQ ID NO:3) sample was 0%, thereby indicating that $\beta$-purothionin (SEQ ID NO:3) was capable of greatly inhibiting the activity of porcine pancreatic lipase even in such concentration.

Furthermore, in a separate experiment carried out in a similar manner as given above, $\beta$-purothionin (SEQ ID NO:3) was able to reduce the activity of porcine pancreatic lipase to 5.2% even in its concentration of 0.04 mg/ml representing its great inhibitory activity of porcine pancreatic lipase.

EXAMPLE 3

Preparation of Cholesterol Oleate Emulsion 32.5 mg of cholesterol oleate and 25 mg of phosphatidylcholine and 21.5 mg of sodium cholate were added to 5 ml of the potassium phosphate buffer. The solution was ultrasonicated to prepare a cholesterol oleate emulsion.

Preparation of Protein-containing Solution

Following the same procedure as in Example 1, four protein-containing solutions were prepared, each of which contains the crude purothionins, BSA, β-lactoglobulin or ovalbumin.

Preparation of Cholesterol Esterase Solution

A cholesterol esterase isolated from porcine pancreas was added to a 300 mM potassium phosphate buffer solution to prepare an enzyme solution containing 40 μg/ml of cholesterol esterase.

Assay of Cholesterol Esterase Inhibitory Activity of Protein

The control and four test samples were prepared in the following manner.

100 μl of an olive oil emulsion as prepared above were used as a substrate.

50 μl of potassium phosphate buffer was added to the substrate to prepare an emulsion for control sample. Each 50 μl of the protein(polypeptide)-containing solutions as prepared above was added to 100 μl of the substrate to prepare four emulsions for test sample. All of the emulsions were incubated for 5 min. To each of those emulsions was added 50 μl of the lipase solution as prepared above. The resulting mixture was incubated at 37° C. for one hour, subsequently to which were added 3 ml of the same extraction solvent as used in Example 1. After being shaken for 5 min., the mixture was centrifuged at 3000 rpm for 5 min. The upper layer was removed with an aspirator and to the remaining solution was added 1 ml of the same copper reagent as used in Example 1. The mixture was shaken for 5 min. and centrifuged at 3000 rpm for 5 min. 0.5 ml of a solution was taken from the upper layer and to the solution was added 0.5 ml of the same color developing agent as used in Example 1.

The resulting solutions for control and test samples were measured for the absorbance at 480 nm (A480) using a photometer to determine the amount of the free fatty acids as formed, i.e., the activity of the cholesterol esterase.

The results are shown in Table 2 in which the activity is expressed in terms of the percentage of the Abs480 in the case where control sample was hydrolyzed by cholesterol esterase.

TABLE 2

| Protein (polypeptide) contained in samples | Activity of cholesterol esterase (%) |
| --- | --- |
| Control | 100 |
| Crude purothionins (SEQ ID NOS: 1-3) | 9.8 |
| Ovalbumin | 93.6 |
| β-Lactoglobulin | 89.9 |
| BSA | 120.0 |

From the results shown in Table 2, it is seen that the cholesterol esterase activity is much inhibited when the inhibitor of the invention comprising crude purothionins (SEQ ID NOS:1-3), i.e., basic protein was added in the presence of a bile acid, whereas ovalbumin, β-lactoglobulin and BSA, not belonging to basic proteins have no or a little, if any, cholesterol esterase inhibitory activity under this condition.

EXAMPLE 4

Preparation of Olive Oil Emulsion 250 mg of an olive oil, 21.5 mg of sodium cholate as a bile acid component and 30 mg of phosphatidylcholine were added to 5 ml of a 200 mM Tris buffer solution at pH 6.8 (called hereafter "Tris buffer").

The mixture was ultrasonicated to prepare an olive oil emulsion.

Preparation of protein- or peptide-containing solution 10 ml of Tris buffer was added to each 1 mg of the same purified β-purothionin (SEQ ID NO:3) as used in Example 1, protamine (P4005, Sigma Co., Ltd., U.S.A.), histone H2A (H6881, Sigma Co., Ltd.), histone H3 (H4380, Sigma Co., Ltd.), α-poly-L-lysine (3075, Peptide Research Co., Ltd.) and poly-L-arginine (P3892, Sigma Co., Ltd.) to prepare six kinds of protein- or peptide-containing solutions.

Preparation of Lipase Solution

Porcine pancreatic lipase (manufactured by Sigma Co., Ltd.) was added to Tris buffer to prepare an enzyme solution containing 100 units porcine pancreatic lipase per ml.

Assay of Lipase Inhibitory Activity of Proteins

The control and six test samples were prepared in the following manner.

100 μl of an olive oil emulsion as prepared above were used as a substrate.

50 μl of Tris buffer was added to the substrate to prepare an emulsion for control sample. Each 50 ml of the protein(polypeptide)-containing solutions as prepared above was added to 100 μl of the substrate to prepare six emulsions for test sample. All of the emulsions were incubated for 5 min. To each of those emulsions was added 50 μl of the lipase solution as prepared above. The resulting mixture was incubated at 37° C. for one hour, subsequently to which were added 3 ml of the same extraction solvent as used in Example 1. After being shaken for 5 min., the mixture was centrifuged at 3000 rpm for 5 min. The upper layer was removed with an aspirator and to the remaining solution was added 1 ml of the same copper reagent as used in Example 1. The mixture was shaken for 5 min. and centrifuged at 3000 rpm for 5 min. 0.5 ml of a solution was taken from the upper layer and to the solution was added 0.5 ml of the same color developing agent as used in Example 1.

The resulting solutions for control and test samples were measured for the absorbance at 480 nm (A480) using a photometer to determine the amount of the free fatty acids as formed, i.e., the activity of the porcine pancreatic lipase.

The results are shown in Table 1 in which the activity is expressed in terms of the percentage of the Abs480 in the case where control sample was hydrolyzed by the porcine pancreatic lipase.

TABLE 3

| Protein (polypeptide) contained in samples | Isoelectric pH | Activity of porcine pancreatic lipase (%) |
| --- | --- | --- |
| Control | — | 100 |
| α-Purothionin (SEQ ID NO: 3) | Ca. 10 | 1.3 |
| Protamine | Ca. 10 | 1.3 |
| Histone H2A | Ca. 10 | 3.7 |
| Histone H3 | Ca. 10 | 2.3 |
| β-Poly-L-lysine | Ca. 10 | 6.9 |

TABLE 3-continued

| Protein (polypeptide) contained in samples | Isoelectric pH | Activity of porcine pancreatic lipase (%) |
|---|---|---|
| Poly-L-arginine | Ca. 10 | 16.5 |

From the results shown in Table 3 it is seen that the activity of lipase is much inhibited when the inhibitor of the present invention comprising purified β-purothionin (SEQ ID NO:3), protamine, histone, α-poly-L-lysine or poly-L-arginine, a kind of basic protein or peptide was added under the specified condition in this example.

EXAMPLE 5

Two groups of 10 SD male rats (9 weeks age, 200 g average bodyweight) were prepared.

50 g of corn oil, 6 g of yolk lecithine and 12.5 g of glycerol were added to distilled water to make up to 100 ml. The mixture was ultrasonicated to prepare an emulsion.

The rats of first group were each given 2 ml of the emulsion and 100 mg of ε-poly-L-lysine manufactured by Chisso Corp. [containing dextrin and ε-poly-L-lysine at a weight ratio of 1:1 and having formula (I) wherein n is ca. 30], orally using a gastric probe. Blood was drawn at predetermined intervals from the tail vein, and serum triglyceride concentration was measured using Kyowa Medics enzyme Kit TG, determined for mean value (mg/dl) per animal and calculated on the basis of serum triglyceride concentration prior to administration (taken as 0 mg/dl) (According to the invention).

The rats of second group were orally given 2 ml of the emulsion and 50 mg of dextrin. Serum triglyceride concentration was measured at predetermined intervals, determined for the average value and calculated in the same way as above (Comparative example).

The results are shown in Table 4 below.

TABLE 4

| Elapsed time after administration (hrs.) | Blood concentration of neutral fats (ml/dl) | |
|---|---|---|
| | Inventive | Comparative |
| 0 (before administration) | 0 | 0 |
| 1 | 53.3 ± 2.5$^a$ | 176.8 ± 16.3 |
| 2 | 32.4 ± 4.9$^a$ | 124.1 ± 25.2 |
| 3 | 16.7 ± 3.2$^a$ | 79.6 ± 11.0 |
| 4 | 11.1 ± 3.0$^a$ | 62.0 ± 10.5 |
| 7 | 4.2 ± 1.0$^a$ | 17.3 ± 3.0 | a: Significantly different at P < 0.01

As seen from the results in Table 4, in the case where the rats are given a test sample containing ε-poly-L-lysine (a basic peptide of the invention), the intestinal lipid absorption is inhibited and serum triglyceride concentration can be controlled at a low level over a period of time from the beginning to as far as 7 hours after administration, resulting in largely reduced total fat absorption. These results indicate that ε-polylysine has an inhibitory activity in vivo against lypolytic enzyme over a long period of time.

EXAMPLE 6

Preparation of Peptide-containing Solutions

Two peptide-containing solutions were prepared by adding 1 ml of distilled water to each 1 mg of α-poly-L-lysine hydrochloride (3075, Peptide Research Co., Ltd.) and α-poly-D-lysine hydrobromide (P7886, Sigma Co., Ltd.).

Assay of Lipase Inhibitory Activity of Polylysine

The control and two test samples were prepared in the following manner.

100 μl of an olive oil emulsion prepared in the same way as in Example 4 were used as a substrate.

50 μl of Tris buffer was added to the substrate to prepare an emulsion for control sample. Each 50 μl of the polypeptide-containing solutions as prepared above was added to 100 μl of the substrate to prepare two emulsions for test sample. After incubating the emulsions for 5 min., there was added 50 μl of the enzyme solution prepared in the same way as in Example 4. The resulting mixture was incubated at 37° C. for one hour.

Further, the incubated mixture was treated and measured for the activity of porcine pancreatic lipase in the same way as in Example 4.

TABLE 5

| Polylysine contained in samples | Activity of porcine pancreatic lipase |
|---|---|
| Control | 100 |
| α-Poly-L-lysine hydrochloride | 1.6 |
| α-Poly-D-lysine hydrobromide | 1.1 |

It is seen from the above data that both L and D polylysines can greatly inhibit the lipase activity under the specified condition in this example.

EXAMPLE 7

Preparation of Peptide-containing Solutions

Lysine oligomers having a degree of polymerization of 2–5 as shown in Table 6 below were prepared using a peptide synthesizer (Biolynx 4170, LKB-Pharmacia Co., Ltd.). Each of the oligomers was purified by high performance liquid chromatography. Each of the purified oligomers was added to distilled water to make up to 1 μmol/ml. Seven lysine oligomer-containing solutions were thus prepared.

Assay of Lipase Inhibitory Activity of Lysine Oligomers

The control and six test samples were prepared in the following manner.

100 μl of an olive oil emulsion prepared in the same way as in Example 4 were used as a substrate.

50 μl of Tris buffer was added to the substrate to prepare an emulsion for control sample. Each 50 μof the lysine oligomer-containing solutions as prepared above was added to 100 μl of the substrate to prepare six emulsions for test sample. After incubating the emulsions for 5 min., there was added 50 μl of a lipase solution containing 100 units of porcine pancreatic lipase per ml as prepared in the same way as in Example 4. The resulting mixture was incubated at 37° C. for one hour.

Further, the incubated mixture was treated and measured for the activity of porcine pancreatic lipase in the same way as in Example 4.

The results are shown in Table 6.

TABLE 6

| Lysine oligomer contained in samples | Activity of porcine pancreatic lipase (%) |
|---|---|
| Control | 100 |
| α-(L-lysine)$_2$ | 103.6 |
| α-(L-lysine)$_4$ (SEQ ID NO: 4) | 103.8 |
| α-(L-lysine)$_5$ (SEQ ID NO: 5) | 2.1 |
| ε-(L-lysine)$_3$ | 89.0 |
| ε-(L-lysine)$_4$ (SEQ ID NO: 6) | 53.8 |

TABLE 6-continued

| Lysine oligomer contained in samples | Activity of porcine pancreatic lipase (%) |
| --- | --- |
| ε-(L-lysine)₅ (SEQ ID NO: 7) | 3.1 |

As seen from the above data, lysine oligomers of α type with the polymerization degree of 5 or more strongly inhibit lipase activity, whereas the oligomers with the polymerization degree of 4 or below have no lipase inhibitory activity at all under the specified in this example. Further, lysine oligomers of ε type with the polymerization degree of 4 (SEQ ID NO:6) have a lipase inhibitory activity but not high enough, whereas the oligomer with the polymerization degree of 5 (SEQ ID NO:7) has very high lipase inhibitory activity. It is understood from Table 6 that lysine oligomer with higher degree of polymerization has greater lipase inhibitory activity than lower polymerized lysine.

It is reported that ε-lysine oligomers with the polymerization degree of about 10 or higher possess strong antimicrobial property. From such report and the results shown in Table 6 it is anticipated that ε-lysine oligomers having the polymerization degree of 5–9 which will produce no adverse effect upon intestinal flora can be used more effectively as a lipolytic enzyme inhibitor.

---

What is claimed is:

1. A method of inhibiting enzymatic hydrolysis of lipids in the gastro-intestinal system of a mammal, comprising orally administering an effective amount of a purothionin or a salt thereof to a mammal in need thereof.

2. The method of claim 1, wherein the purothionin is $\alpha_1$-purothionin (SEQ ID NO:1), $\alpha_2$-purothionin (SEQ ID NO:2), $\beta$-purothionin (SEQ ID NO:3) or a salt thereof.

3. The method of claim 1, wherein said purothionin or salt thereof are present in a composition further containing a biologically acceptable carrier, wherein said purothionin or salt thereof are present in an amount of from 0.1 to 4 mg per 1 ml of the biologically acceptable carrier.

4. A method of inhibiting enzymatic hydrolysis of lipids in the gastro-intestinal system of a mammal, comprising orally administering an effective amount of an $\epsilon$-polylysine of the formula:

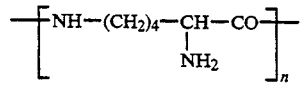

or a salt thereof, wherein n is a number of from 5 to 9, to a mammal in need thereof.

5. The method of claim 4, wherein the salt of $\epsilon$-polylysine is $\epsilon$-poly-L-lysine hydrochloride or $\epsilon$-poly-D-lysine hydrobromide.

6. A method of inhibiting enzymatic hydrolysis of lipids in the gastro-intestinal system of a mammal, comprising orally administering an effective amount of an $\epsilon$-polylysine of the formula:

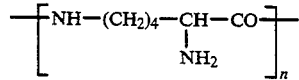

or a salt thereof, wherein n is a number of from 4 to 30, to a mammal suffering from lipemia or obesity.

7. The method of claim 6, wherein the salt of $\epsilon$-polylysine is $\epsilon$-poly-L-lysine hydrochloride or $\epsilon$-poly-D-lysine hydrobromide.

* * * * *